United States Patent [19]
Akazawa

[11] Patent Number: 5,737,937
[45] Date of Patent: Apr. 14, 1998

[54] ACCESSORY STRUCTURE FOR SPRAY CLEANING A HEAT EXCHANGER IN A VEHICLE AIR-CONDITIONER

[76] Inventor: Yasumasa Akazawa, 2-8-14, Higashishinmachi, Matsubara, Osaka, Japan

[21] Appl. No.: 740,159

[22] Filed: Oct. 28, 1996

[51] Int. Cl.$^6$ ................................................. F28G 9/00
[52] U.S. Cl. ................................................. 62/303; 165/95
[58] Field of Search ........................ 62/303, 305, 237, 62/239, 78, 244, 310; 165/41, 95

[56] References Cited

U.S. PATENT DOCUMENTS 3,926,000 12/1975 Scofield ................................. 62/244

Primary Examiner—John M. Sollecito
Attorney, Agent, or Firm—Moonray Kojima

[57] ABSTRACT

The present invention relates to an accessory structure for vehicle air-conditioner for improving the compartment atmosphere by cleaning the evaporator as heat exchanger and others or feeding aromatic or other functional solvent in a vehicle air-conditioner for taking in external air or internal air from an air-conditioning air intake route, and more particularly to an accessory structure for vehicle air-conditioner capable of improving the compartment atmosphere, by connecting a solvent feed route to solvent flow injection means provided at the upstream side of the heat exchanger in the air-conditioning air intake route, providing the base end of the solvent feed route with receiving means separated from the solvent source, fixing the receiving means in a specific place in the compartment, and putting in an accommodating space such as glove box, while separating the solvent source such as filled container from the receiving means, thereby preventing the solvent source from being ruptured or damaged, and moreover by receiving the solvent from the solvent source when necessary by the receiving means corresponding to the type of solvent, thereby cleaning the heat exchanger or feeding aromatic or other functional solvent.

16 Claims, 6 Drawing Sheets

ACCESSORY STRUCTURE FOR SPRAY CLEANING A HEAT EXCHANGER IN A VEHICLE AIR-CONDITIONER

BACKGROUND OF THE INVENTION

1. Field of the Invention

The present invention relates to an accessory structure for vehicle air-conditioner for improving the compartment atmosphere by cleaning the evaporator as heat exchanger and others or feeding aromatic or other functional solvent in a vehicle air-conditioner for taking in external air or internal air from an air-conditioning air intake route.

2. Description of the Prior Art

To improve the compartment atmosphere by cleaning the evaporator or feeding aromatic or other functional solvent as described above, a solvent spray nozzle is provided at the upstream side of the heat exchanger in the air-conditioning air intake route, a hose communicating with this nozzle is led out into the compartment, and a container filled with solvent put in a case is installed near the driver's seat or front seat, and a base end of the hose is fitted to the solvent discharge port of the filled container. However, if the filled container is placed near the driver's seat or front seat, since the filled container is intended to obtain a discharge force of the solvent by sealing with packed gas, the filled container may be ruptured in case the packed gas is overheated by exposure to direct sunlight or elevation of compartment temperature.

SUMMARY OF THE INVENTION

It is hence a primary object of the invention to present an accessory structure for vehicle air-conditioner capable of improving the compartment atmosphere by cleaning the heat exchanger or feeding aromatic or other functional solvent, by connecting a solvent feed route to solvent flow injection means provided at the upstream side of the heat exchanger in the air-conditioning air intake route, providing the base end of the solvent feed route with receiving means separated from the solvent source, fixing the receiving means in a specific place in the compartment, and putting in an accommodating space such as glove box and console box not heated to high temperature, while separating the solvent source such as filled container from the receiving means, thereby preventing the solvent source from being ruptured or damaged, and moreover by taking out the solvent source from the accommodating space, when using, and inserting the nozzle into the nozzle guide.

It is other object of the invention to present an accessory structure for vehicle air-conditioner capable of feeding the solvent adequately, by providing the receiving means with a guide for positioning the nozzle of the solvent source when feeding the solvent, so that the nozzle of the solvent source may be positioned at the guide of the receiving means.

It is a different object of the invention to present an accessory structure for vehicle air-conditioner capable of improving the controllability, by forming a taper in the guide, so that the nozzle may be guided into the optimum position for feeding solvent by the taper if the nozzle of the solvent source is brought close to the guide from an oblique direction.

It is a further object of the invention to present an accessory structure for vehicle air-conditioner capable of preventing counterflow of solvent securely, by disposing counterflow preventive means between the guide and the base end portion of the solvent feed route.

It is a further different object of the invention to present an accessory structure for vehicle air-conditioner capable of preventing dust and foreign mater from sticking and invading into the solvent passage of the guide, by disposing closing means for closing the solvent passage of the guide in the inner side of a lid member for covering the guide.

Other objects of the invention will be easily clarified from the description of the embodiments described below.

DESCRIPTION OF THE PREFERRED EMBODIMENTS

[Embodiments]

An embodiment of the invention is described in detail below while referring to drawings.

Figure 1:
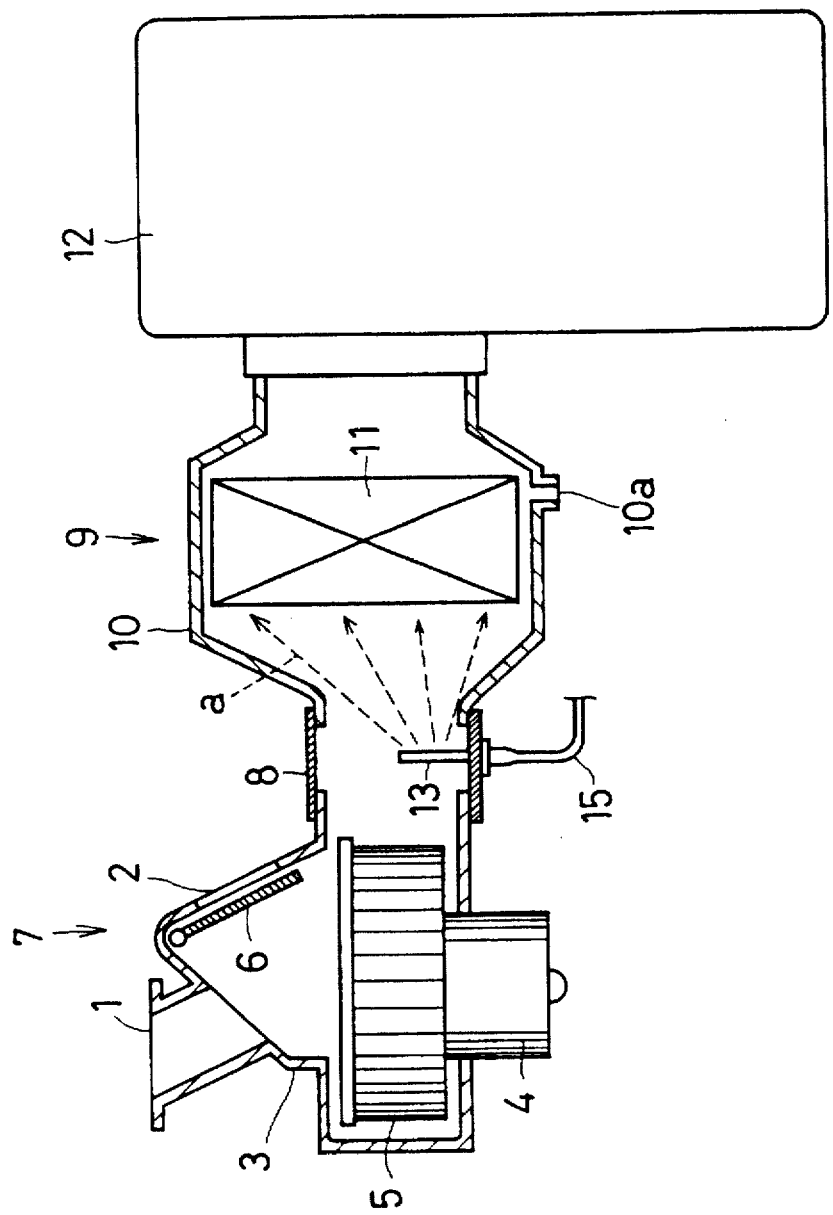
FIG. 1 is a side view showing an accessory structure for vehicle air-conditioner of the invention.

The drawings show an accessory structure for vehicle air-conditioner, and first describing the constitution of the vehicle air-conditioner, in FIG. 1, an internal/external air changeover box 3 having an external air intake port 1 and an internal air intake port 2 is provided, and a fan 5 driven by a blower motor 4 is disposed in the box 3, together with an internal/external air changeover door 6 for selecting intake of air-conditioning air.

In a next stage of thus composed blower unit 7, a cooler unit 9 is disposed through a communication duct 8. The cooler unit 9 incorporates an evaporator 11 as heat exchanger in a cooler housing 10. A drain port 10a is formed in the cooler housing 10 immediately beneath the evaporator 11.

The evaporator 11 is an evaporating device connected in a refrigerating cycle, and acts to deprive the surrounding of heat.

In a next stage of the cooler unit 9, a heater control unit 12 is connected to communicate. Inside this unit 12, there are a heater core, an air mixing door, a vent door, a defroster door, a heat door, and a mixing chamber, and by changeover of these doors, air-conditioned air (cool air or warm air) is blown out into necessary positions in the compartment from the defroster outlet, vent outlet, and heat outlet.

In thus constituted vehicle air-conditioner, as an example of air-conditioned air intake route, the communication duct 8 positioned at the upstream side of the evaporator 11 is provided with a nozzle 13 for injecting a solvent fluid (a) toward the nearly entire region of the front side of the evaporator 11.

Figure 2:
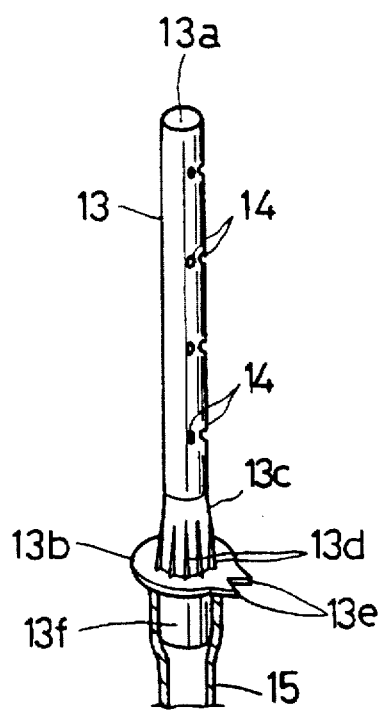
FIG. 2 is a perspective view of a nozzle.

The nozzle 13 is a relatively slender cylindrical form made of synthetic resin having a closed leading end 13a as shown in FIG. 2, and injection ports 14, 14 in twin structure are pierced in the positions confronting the front surface of the evaporator 11 as indicated in the dotted line arrow direction in FIG. 1.

A nozzle neck 13c near the flange 13b is formed in a taper tube smaller in diameter at the leading end 13a side and larger in diameter at the flange 13b side, and plural protrusions 13d... of triangular cross section inserted and stopped in the rubber communication duct 8 are formed integrally on its outer circumference. Accordingly, only by piercing pores in the communication duct 8, the nozzle 13 can be mounted instantly and securely. Of course, bonding means for bonding the flange 13b to the communication duct 8 may be also employed.

Still more, in the flange 13b, a protrusion for marking at the time of mounting nearly coinciding with the injection direction of the solvent fluid (a) is formed integrally, so that the nozzle 13 may be directed and mounted in correct direction by preventing mounting direction error of the nozzle 13 when mounting the nozzle 13. The leading end of the rubber hose 15 (solvent feed route) is adhered and fixed to the joint 13f in the nozzle 13 by making use of its elastic tightening force (elastic restoring force).

Figure 3:
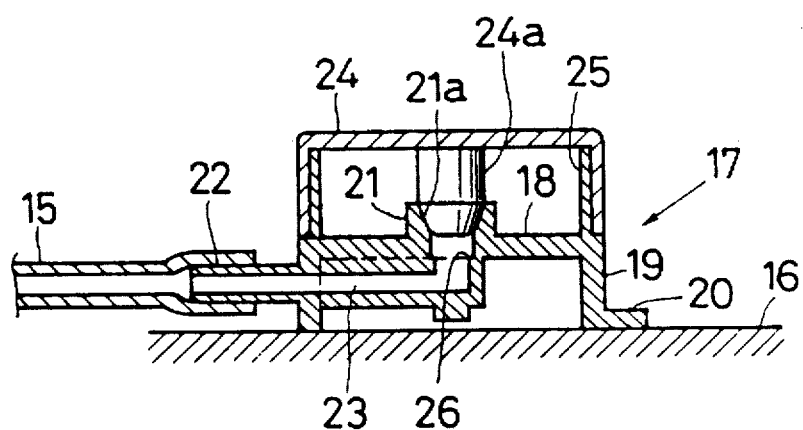
FIG. 3 is a sectional view of a receiving member.

The base end side of the rubber hose 15 is led out into the compartment is coupled to communicate with a receiving member 17 made of synthetic resin as receiving means fixed at a specific place near the driver's seat or front seat as shown in FIG. 3, for example, in a specific place at the front, side or bottom of an instrument panel 16 by proper means (adhering, bolting, clipping, or taping with double-sided adhesive tape).

The receiving member 17 is completely separated and isolated from a filled container A of solvent as solvent source (see FIG. 6), and its specific constitution is as shown in FIG. 3 to FIG. 6.

That is, a flange 20 is integrally formed in a main plate 18 through a ring-shaped spacer 19, and a solvent passage 23 is formed between a guide 21 of a nearly cylindrical form provided in the middle of the main plate 18 and a joint 22 projecting outward from part of outer circumference of the spacer 19, while a ring-shaped holder 25 for supporting a lid member 24 is integrally formed at the anti-spacer 19 side in the main plate 18, thereby composing the main body side of the receiving member 17.

The guide 21 is intended to position the nozzle N (see FIG. 6) of the filled container A (a handy type container packed with gas) to be inserted when feeding the solvent, and a taper 21a larger in diameter at the outward side and smaller in diameter at the inward side is formed in the guide 21, and an annular step 26 for preventing excessive insertion of the nozzle N is formed at the inner side of the taper 21a.

Figure 5:
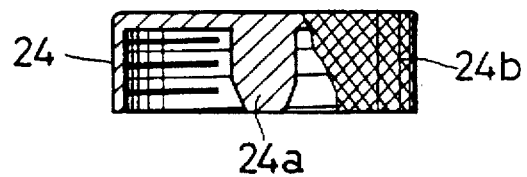
FIG. 5 is an explanatory diagram of the lid member.

The lid member 24 is detachably screwed into a holder 25, and inside of the lid member 24, a protrusion 24a as closing means for closing the solvent passage 23 of the guide 21, more specifically, the taper 21a is formed integrally, and the outer circumference of the lid member 24 is roughly processed so as to facilitate detaching and attaching of the member 24. In FIG. 5, as an example of rough processing, a knurled portion 24b is shown, but other rough processing may be also done.

Figure 4:
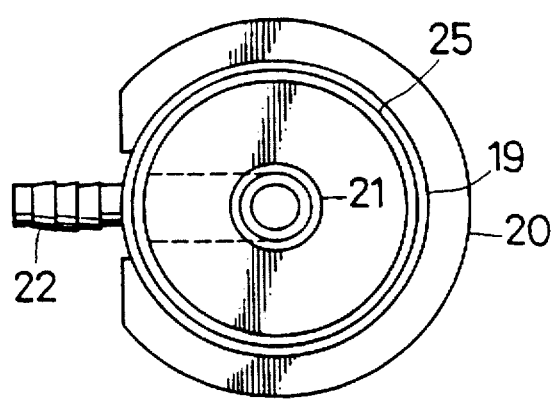
FIG. 4 is a plan view of a receiving member in a lid member removed state.

The outer shape of the joint 22 is formed in detent shape by taper cone multiple structure as shown in FIG. 4, and the base end of the rubber hose 14 is fitted and fixed to the joint 22 by effectively utilizing its elastic tightening force.

In this way, by completely separating and isolating the receiving member 17 from the handy type filled container A, the filled container A can be put in the glove box or console box of the vehicle.

Herein, usable examples of the solvent fluid (a) include, among others, liquid detergent, foamy cleaning solution (water, phosphoric acid, Softanol 70, propylene glycol monomethyl ether MGF, and others properly blended), cleaning water, aromatics, chemicals, deodorant, deodorizer, disinfectant, antibacterial, bactericide, and fungicide, which may be used either alone or in mixture (compound). For aromatic effect in the compartment alone, only a filled container packed with aromatic solvent may be used.

Elements 13, 14, 15, 17 shown in FIG. 2 are handled as a kit, and the elements 13 to 15, 17 may be additionally attached to the vehicle, or may be formed integrally when manufacturing the vehicle.

The action of the accessory structure for vehicle airconditioner thus constituted is described below.

Figure 6:
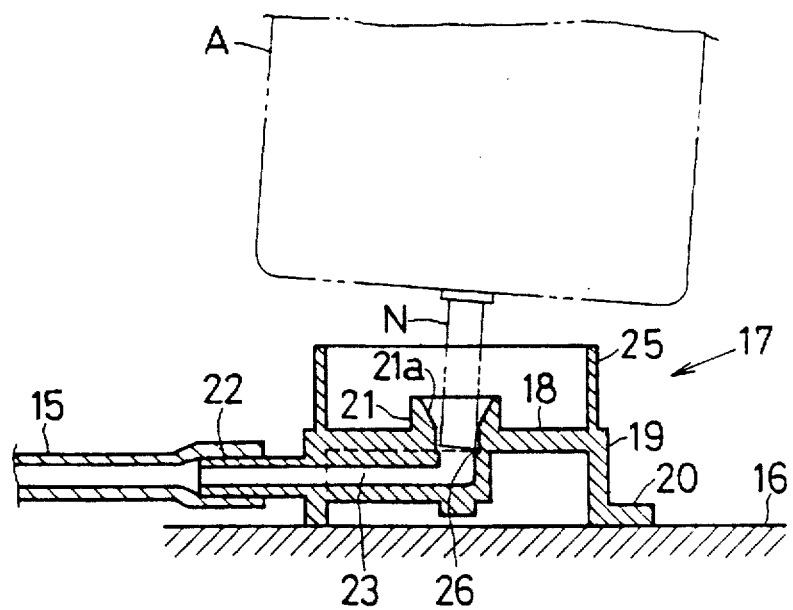
FIG. 6 is an explanatory diagram of solvent feeding.

When cleaning the evaporator 11, after detaching the lid member 24 from the receiving member 17 shown in FIG. 3, the nozzle N of the filled container A is inserted into the solvent passage 23 while being guided by the taper 21a of the guide 21 as shown in FIG. 6, and the cleaning fluid is pressed out from the nozzle N, and then the cleaning fluid is supplied into the rubber hose 15 through the solvent passage 23 and flows into the nozzle 13 from the leading end, and is injected from multiple injection ports 14 ... toward the nearly entire area of the front surface of the evaporator 11, so that the fins in complicated shape (not shown) of the evaporator can be cleaned sufficiently almost entirely, and the fluid after cleaning process is discharged from the drain port 10a immediately beneath the evaporator 11. If necessary, a drain hose may be connected to the drain port 10a, and the fluid after cleaning process may be discharged out of the vehicle.

Herein, by driving the fan 5 while injecting the cleaning fluid from the injection ports 14, the cleaning fluid reaches further to the inner parts of the fins in complicated shape, so that the cleaning effect may be further enhanced.

The sequence of use of solvent fluids (a) may be foamy detergent and chemical such as disinfectant or antibacterial in this sequence, or foamy detergent, cleaning water, and chemical in this sequence, or liquid detergent and antibacterial in this sequence, and moreover after cleaning process, the evaporator 11 may be dried by feeding air, warm air, hot air or cold air from the base end opening side of the rubber hose 15.

Figure 7:
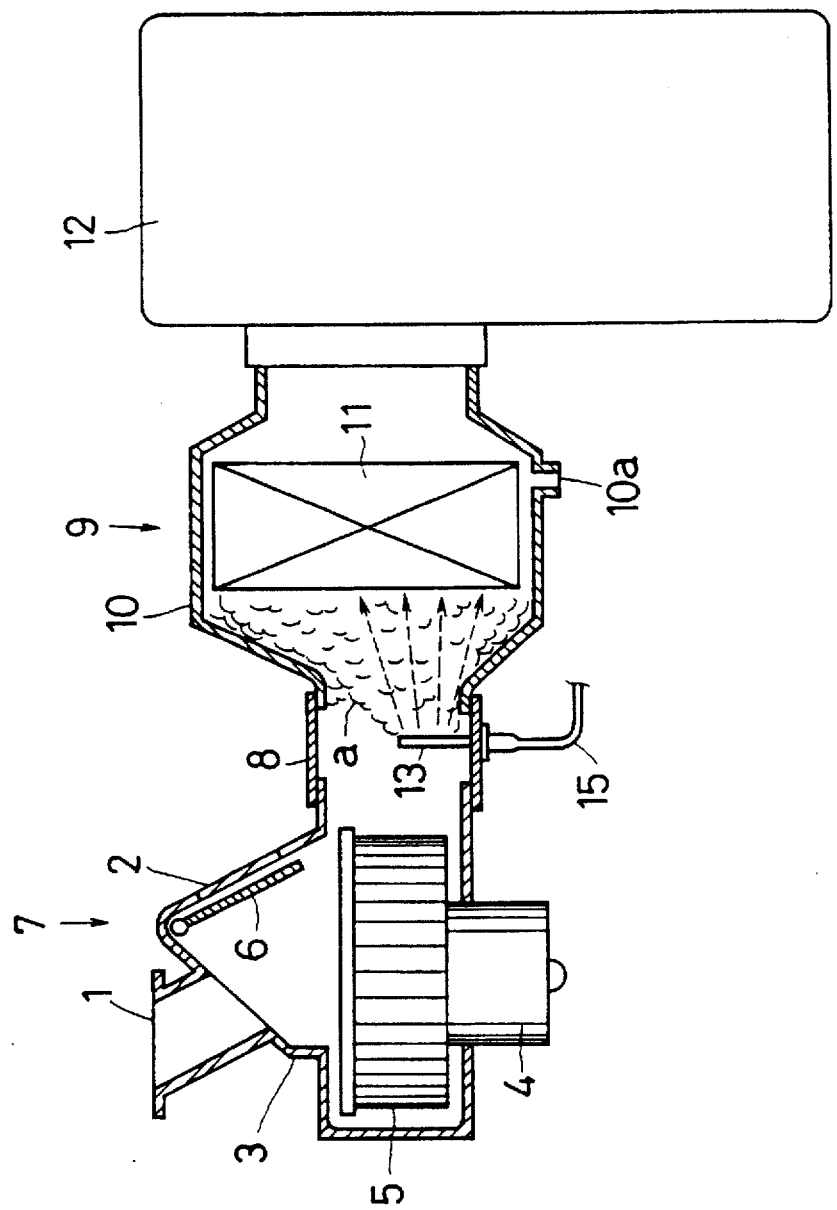
FIG. 7 is an explanatory diagram of use of foamy cleaning fluid.

In particular, when the solvent fluid (a) injected from the nozzle 13 is a foamy cleaning fluid (a), if the dimension of the nozzle 13 is relatively short as compared with the internal overall height of the communication duct 8 as shown in FIG. 7, the foamy cleaning fluid injected from the nozzle 13 is spread over the entire front region (that is, full surface) of the upstream side of the evaporator 11 as shown in FIG. 7 owing to the characteristic of the foamy fluid, and the entire evaporator 11 can be clean efficiently, to the inner parts, by the foamy cleaning fluid by circulation of airconditioning air, and therefore the nozzle 13 is compact in size, and mounting of the nozzle 13 on the vehicle airconditioner may be further easier.

In short, the rubber hose 15 is connected to the nozzle 13 provided at the upstream side of the evaporator 11 in the air-conditioning air intake route (the route from air intake ports 1, 2 to the evaporator 11), the receiving member 17 separated from the packed solvent A is provided at the base end of the rubber hose 15, and the receiving member 17 is fixed in a specific place in the compartment, and therefore the solvent source such as filled container A is separated from the receiving member 17 and can be put in an accommodating space, for example, glove box or console box, not heated to high temperature, so that rupture or damage of the solvent source may be prevented. At the time of use, the solvent container A is taken out from the accommodating space, and is inserted into the nozzle guide, and the evaporator 11 is cleaned, or aromatic or other functional solvent is supplied, so that the compartment atmosphere may be improved.

As the solvent fluid (a), since liquid detergent, foamy detergent, mixed compound detergent of aromatic and deodorant, aromatics, deodorant, deodorizer, disinfectant, antibacterial, bactericide, fungicide, and other solvents may be used either alone or in mixture, by selection of solvent fluids (a) injected from the nozzle 13, the cleaning function, or aromatic, deodorizing, disinfecting, or fungicidal function may be obtained, thereby cleaning the inside of the air-conditioner, preventing offensive smell, or obtaining bactericidal or fungicidal effect.

Further, since the receiving member 17 is provided with the guide 21 for positioning the nozzle N of the filled container A when feeding the solvent, the solvent an be supplied appropriately by positioning the nozzle N of the filled container a at the guide 212 of the receiving member 17.

Moreover, since the taper 21a is formed in the guide 21, if the nozzle N of the filled container A is brought closer to the guide, this nozzle is guided into the solvent feed optimum position by the taper 21a, so that the controllability may be enhanced.

In addition, the protrusion 24a for closing the solvent passage 23 of the guide 21 is provided inside the lid member 24 for covering at least the guide 21, and it is effective to prevent securely the dust and other foreign matter from sticking or invading to the solvent passage 23 of the guide 21.

Figure 8:
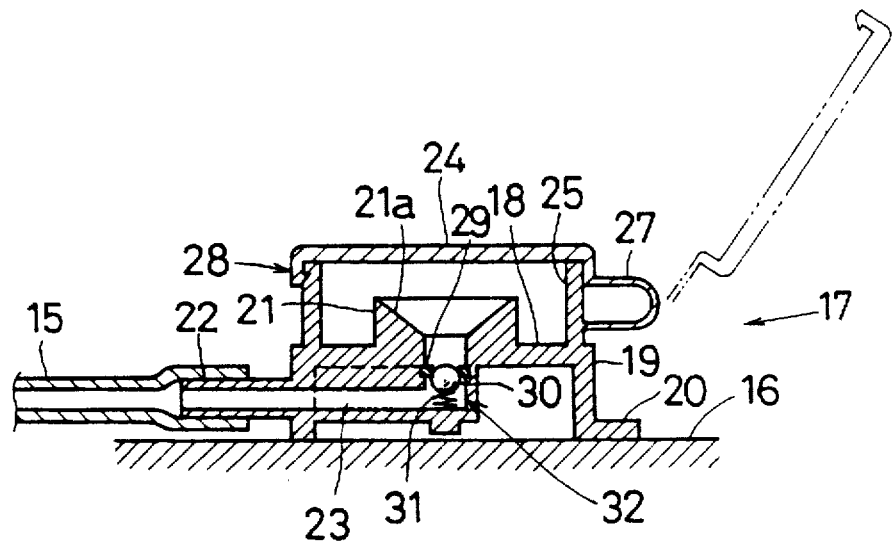
FIG. 8 is a sectional view showing other embodiment of the receiving member.

FIG. 8 shows other embodiment of the receiving member 17, in which the lid member 24 is integrally connected to the ring-shaped holder 25 through an elastic piece 27 in a lateral U form, and these members 24, 25 are detached or attached instantly by the convex and concave fixing means 28 of convex portion formed in the lid member 24 and concave portion formed in the holder 25, thereby enhancing the controllability when closing the lid member 24 and preventing loss of the member 24 when opening the lid member 24.

Still more, in an intermediate portion of the solvent passage 23, a check valve 32 comprising a valve seat 29, a ball valve 30, and a spring 31 having the same function as the annular step 26 is disposed so as to prevent counterflow of the solvent fluid (a).

Thus, since the check valve 32 is provided in the solvent passage 23 between the guide 21 and base end portion of the rubber hose 15, counterflow of the solvent can be securely blocked.

In the embodiment in FIG. 8, too, the other members have nearly same action and effect as in the foregoing embodiment, and same parts as in the preceding drawings are identified with same reference numerals in FIG. 8 and detailed description is omitted.

Figure 9:
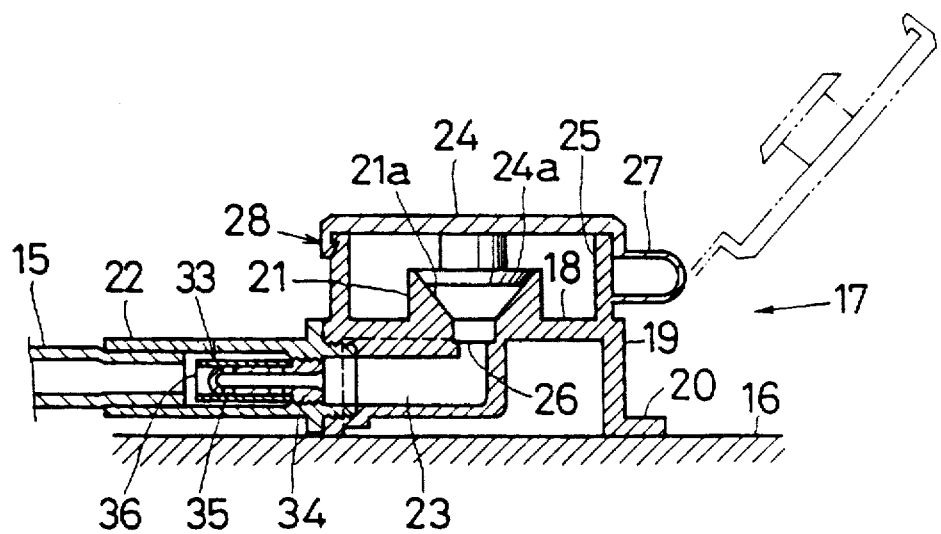
FIG. 9 is a sectional view showing a different embodiment of the receiving member.

FIG. 9 shows a further different embodiment of the receiving member 17, in which the joint 22 is larger in diameter than the one shown in the foregoing embodiments, and is detachable from the spacer 17 by threading, and a counterflow preventive member 33 for preventing counterflow of solvent is detachably disposed in the joint 22.

The counterflow preventive member 33 comprises a pipe member 34 screwed into the joint 22 and closed at the leading end, plural openings 35 pierced in the pipe member 34 for circulating the solvent, and a tube member 36 fitted to the outer circumference of the pipe member 35 and bulging and deforming by the solvent pressure to allow circulation of solvent, in which, when the solvent pressure is released, the openings 35 are closed by contracting by the restoring force of the material of the tube member 36, thereby preventing counterflow.

In this embodiment, the base end portion of the rubber hose 15 is connected to communicate inside the joint 22.

In this way, since the counterflow preventive member 33 is disposed in the solvent passage between the guide 21 and base end portion of the rubber hose 15, counterflow of the solvent can be blocked securely.

In the embodiment in FIG. 9, too, the other members have nearly same action and effect as in the foregoing embodiments, and same parts as in the preceding drawings are identified with same reference numerals in FIG. 9 and detailed description is omitted.

In correspondence between the constitution of the invention and the foregoing embodiments, the air-conditioning air intake route of the invention corresponds to the route from the air intake ports 1, 2 to the evaporator 11 in the embodiments, and similarly thereafter, the heat exchanger, to the evaporator 11, the solvent injection means, to the nozzle 13, the solvent feed route, to the rubber hose 15, the solvent source, to the filled container A, the receiving means, to the receiving member 17, the counterflow preventive means, to the check valve 32,or the counterflow preventive member 33, and the closing means, to the protrusion 24, but it must be noted, however, the invention is not limited to the illustrated embodiments alone.

For example, in FIG. 1 and FIG. 7, the evaporator 11 is disposed in the next stage of the fan 5 in the vehicle air-conditioner, but in the vehicle air-conditioner of the type in which the fan is disposed in the next stage of the evaporator, the nozzle 13 may be provided at the upstream side of the evaporator, so as not to interfere with the rotary locus of the internal/external air changeover door.

In the embodiments, only a set of constituent elements composed of elements 13 to 15 and 17 was used, but using plural sets of constituent elements, the nozzles 13 may be disposed at different positions at the upstream side of the evaporator 11 and upstream side of the fan 5, and the elements 15 and 17 may be used independently for each solvent.

Moreover, the solvent feed route may be, instead of rubber hose 15, resin tube or metal piping, and the structure of the nozzle 13 is not limited to the illustrated embodiments alone. (f) claims

What is claimed is:

1. A cleaning apparatus for a vehicle air conditioner comprising an air intake route, said apparatus comprising:
   at least one injection means disposed at an upstream side of a heat exchanger and in said air intake route for applying a cleaning solvent to clean the heat exchanger;
   a solvent feed route for feeding the cleaning solvent to said at least one injection means; and
   receiving means separate from a solvent source for receiving the cleaning solvent from the solvent source, said receiving means being connected to communicate with a base end of said solvent feed route and being located in said vehicle.

2. The apparatus of claim 1, wherein said receiving means comprises a guide means for positioning said solvent source to feed said cleaning solvent to said solvent feed route.

3. The apparatus of claim 2, wherein said guide means comprises a taper larger in diameter at an outward side and smaller in diameter at an inward side.

4. The apparatus of claim 2, wherein said receiving means comprises a counter flow preventing means disposed between said guide means and said base end of said solvent feed route.

5. The apparatus of claim 2, wherein said receiving means comprises a lid member for covering at least said guide means, and closing means provided inside of said lid member for closing said guide means.

6. The apparatus of claim 1, wherein said receiving means is attached to an interior surface of said vehicle.

7. The apparatus of claim 2, wherein said receiving means is attached to an interior surface of said vehicle.

8. The apparatus of claim 3, wherein said receiving means is attached to an interior surface of said vehicle.

9. The apparatus of claim 4, wherein said receiving means is attached to an interior surface of said vehicle.

10. The apparatus of claim 5, wherein said receiving means is attached to an interior surface of said vehicle.

11. A vehicle air conditioning system comprising:

an air intake means;

a heat exchanger;

a source of cleaning solvent;

injection means disposed at an upstream side of said heat exchanger and in said air intake means for applying a cleaning solvent to clean said heat exchanger;

solvent feeding means for feeding said cleaning solvent to said injection means; and receiving means separate from said source of cleaning solvent for receiving said cleaning solvent from said source and for feeding said cleaning solvent to said solvent feeding means, wherein said receiving means is located in said vehicle.

12. The system of claim 11, wherein said receiving means comprises a guide means for positioning said source of cleaning solvent to feed said cleaning solvent to said solvent feeding means.

13. The system of claim 12, wherein said guide means comprises a taper larger in diameter at an outward side and smaller in diameter at an inward side.

14. The system of claim 12, wherein said receiving means comprises a counter flow preventing means disposed between said guide means and said solvent feeding means.

15. The system of claim 12, wherein said receiving means comprises a lid member for covering at least said guide means, and closing means provided inside of said lid member for closing said guide means.

16. The system of claim 11, wherein said receiving means is attached to an interior surface of said vehicle.

* * * * *